(12) United States Patent
Alhajri et al.

(10) Patent No.: US 10,702,550 B1
(45) Date of Patent: Jul. 7, 2020

(54) SYNTHESIS OF OLIVE LEAF EXTRACT SILVER NANOPARTICLES

(71) Applicant: KING SAUD UNIVERSITY, Riyadh (SA)

(72) Inventors: Hassna Mohammed Alhajri, Riyadh (SA); Wedad Saeed Al-Qahtani, Riyadh (SA); Seham Soliman Al Terary, Riyadh (SA); Bahauddeen M. Alrfaei, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/565,938

(22) Filed: Sep. 10, 2019

(51) Int. Cl.
    *A61K 9/14* (2006.01)
    *A61K 33/38* (2006.01)
    *A61K 36/63* (2006.01)
    *A61P 35/00* (2006.01)

(52) U.S. Cl.
    CPC ............ *A61K 33/38* (2013.01); *A61K 9/14* (2013.01); *A61K 36/63* (2013.01); *A61P 35/00* (2018.01); *A61K 2236/53* (2013.01)

(58) Field of Classification Search
    CPC .......... A61K 9/14; A61K 9/145; A61K 9/143; A61K 9/148; A61K 9/50; A61K 9/5063; A61K 33/38
    See application file for complete search history.

(56) References Cited

U.S. PATENT DOCUMENTS 9,925,229 B1    3/2018  Choksi

FOREIGN PATENT DOCUMENTS

| JP | 2008273938 A | 11/2008 |
|----|--------------|---------|
| WO | 2013162484 A1 | 10/2013 |
| WO | 2014088520 A1 | 6/2014 |

OTHER PUBLICATIONS

Khalil et al (Green synthesis of silver nanoparticles using olive leaf extract and its antibacterial activity; Arabian Journal of Chemistry (2014) 7, 1131-1139) (Year: 2014).*
Benavente et al (Antioxidant activity of phenolic extracted from *Olea europaea* L leaves, Food Chemistry 68, 2000, 457-462) (Year: 2000).*
Hashmi et al (Traditional Uses, Phytochemistry, and Pharmacology of *Olea europaea* (Olive), Evidence Based Complementary and Alternative Medicine, vol. 2015, Article ID 541591). (Year: 2015).*
Fahimirad, S., et al., "Synthesis and therapeutic potential of silver nanomaterials derived from plant extracts," Ecotoxicology and Environmental Safety, 168, pp. 260-278 (2019).
Boss, A., et al., "Evidence to support the anti-cancer effect of olive leaf extract and future directions," Nutrients, 8, 513 (2016).
Fu, S., et al., "Qualitative screening of phenolic compounds in olive leaf extracts by hyphenated liquid chromatography and preliminary evaluation of cytotoxic activity against human breast cancer cells," Analytical and Bioanalytical Chemistry, 397(2), pp. 643-654 (2010).
Garcia-Villalba, R., et al., "Characterized and quantification of phenolic compounds of extra-virgin olive oils with resolutive LC-ESI-TOF MS method," Journal of Pharmaceutical and Biomedical Analysis, 51(2), pp. 416-429 (2010).
Gorzynik-Debicka, M., et al., "Potential health benefits of olive oil and plant polyphenols," International Journal of Molecular Sciences, 19, 547 (2018).
Khan, Y., et al., "Bio-synthesized silver nanoparticles using different plant extracts as anti-cancer agent," Journal of Nanomedicine and Biotherapeutic Discovery, 7(2) (2017).
Mahmoud, A. E., et al., "Antioxidant and anticancer efficacy of therapeutic bioactive compounds from fermented olive waste," Grasas Y Aceites, 69(3), e266 (2018).
Mijatovic S. A., et al., "Multiple antimelanoma potential of dry olive leaf extract," International Journal of Cancer, 128, pp. 1955-1965 (2011).
Morsy, N. F. S., and Abdel-Aziz, M. E., "Efficiency of olive (*Olea europaea* L.) leaf extracts as antioxidant and anticancer agents," Journal of Agroalimentary Processes and Technologies, 20(1), pp. 46-53 (2014).
Panja S., et al., "Biological application of green nanoparticle synthesized from leaf extract of Rauvolfia serpentina Benth," Asian Pacific Journal of Tropical Disease, 6(7), pp. 549-556 (2016).
Shamshoum, H., et al., "Anticancer effects of oleuropein," BioFactors, 43(3) (2017).
Sulaiman, C. M., et al., "Biogenic synthesis of copper oxide nanoparticles using Olea europaea leaf extract and evaluation of their toxicity activities: An In vivo and In vitro study," Biotechnology Progress, 34(1), 218-230.
Tavolaro, P., et al., "Anticancer activity modulation of an innovative solid formulation of extra virgin olive oil by cultured zeolite scaffolds," Food and Chemical Toxicology, 124, pp. 139-150 (2019).
Awwad et al., "Biosynthesis of silver nanoparticles using Olea europaea leaves extract and its antibacterial activity," Nanoscience and Nanotechnology, 2(6), pp. 164-170 (2012).

* cited by examiner

*Primary Examiner* — Micah Paul Young
(74) *Attorney, Agent, or Firm* — Richard C. Litman; Nath, Goldberg & Meyer

(57) ABSTRACT

The olive leaf extract silver nanoparticles may be synthesized by extracting olive leaves and using the extract to synthesize AgNPs. Olive leaves may be washed, dried, and ground to a powder. The olive leaf powder may be mixed with a first solvent to form a first olive leaf extract. The first olive leaf extract may then be separated and/or concentrated by centrifugation and filtration to form a filtrate. The filtrate may be evaporated to form a residue. The residue may then be resuspended in ethanol to form a second olive leaf extract. The second olive leaf extract may be mixed with $AgNO_3$ to form a mixture including the AgNPs.

11 Claims, 6 Drawing Sheets
(1 of 6 Drawing Sheet(s) Filed in Color)

SYNTHESIS OF OLIVE LEAF EXTRACT SILVER NANOPARTICLES

BACKGROUND

1. Field

The disclosure of the present patent application relates to nanotechnology, and particularly, to olive leaf extract silver nanoparticles and their anti-cancer activity.

2. Description of the Related Art

Recently, metal nanoparticles have demonstrated important uses in a variety of fields. In particular, silver nitrate derived nanoparticles have been of interest to researchers, due to their wide range of applications including electronics, biosensing, plasmonics, optics, and medicine.

Synthesis of silver nanoparticles (AgNPs) has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce byproducts that pose increased risks to human health and the environment.

In recent years, green or environmentally friendly chemical methods have been developed to prepare silver nanoparticles using plant extracts. Green chemistry has the advantage of being fast, environmentally friendly, and economical.

Natural polyphenols derived from olive are gaining importance in recent decades owing to their multitude of beneficial roles in the human system. Polyphenols derived from olive tree (Olea europaea) were reported to have antioxidant, anti-inflammatory, anti-allergic, anti-atherogenic, anti-thrombotic, and anti-tumorigenic properties (Mahmoud et al., 2018). Olive leaf extracts contain phenolic compounds, such as oleuropein, oleuropein aglycon, ligstroside aglycon, oleocanthal, tyrosol, hydroxytyrosol, and many other bioactive compounds have been shown to provide antioxidant, anti-atherogenic, and anticancer properties (Gorzynik-Debicka et al., 2018). There is growing evidence supporting beneficial effects of olive leaf extracts in cancers and other inflammatory diseases (Boss et al., 2016, Mijatovic et al., 2011). The underlying mechanism of these polyphenols has mostly been attributed to its potent antioxidant properties mediated through scavenging of free radicals, thereby preventing oxidative tissue damage. Oleuropein, one of the potent phenolic compounds in olive leaf extracts, was reported to display anticancer activity in several human cancer cell lines, such as MCF-7, RPMI-7951, T-24, HT-29, TF1, A549, LN 18 and A172. The underlying mechanism of oleuropein is thought to be inhibition of proliferation of cancer cell lines, decreasing cell viability, and triggering apoptosis. The anticancer effect of oleuropein is attributed to hydroxytyrosol, the primary metabolite of oleuropein (Shamshoum et al., 2017).

Thus, olive leaf extract silver nanoparticles solving the aforementioned problems are desired.

SUMMARY

Olive leaf extract silver nanoparticles may be synthesized by extracting olive leaves and using the extract to synthesize AgNPs. Olive leaves may be washed, dried, and ground to a powder. The olive leaf powder may be mixed with a solvent to form a first olive leaf extract. The first olive leaf extract may then be separated and/or concentrated by centrifugation and filtration to form a filtrate. The filtrate may be evaporated to form a residue. The residue may then be suspended in ethanol to form a second olive leaf extract. The second olive leaf extract may be mixed with $AgNO_3$ to form a mixture including the AgNPs. In an embodiment, the olive leaves may be olive leaves grown in the Al-Jouf region of Saudi Arabia.

An embodiment of the present subject matter is directed to a pharmaceutical composition including the olive leaf AgNPs and a pharmaceutically acceptable carrier.

An embodiment of the present subject matter is directed to a method of making a pharmaceutical composition including mixing the olive leaf AgNPs under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of treating cancer, including administering to a subject in need thereof a therapeutically effective amount of a pharmaceutical composition according to the present subject matter.

These and other features of the present disclosure will become readily apparent upon further review of the following specification and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Similar reference characters denote corresponding features consistently throughout the attached drawings.

DETAILED DESCRIPTION OF THE PREFERRED EMBODIMENTS

Figure 1:
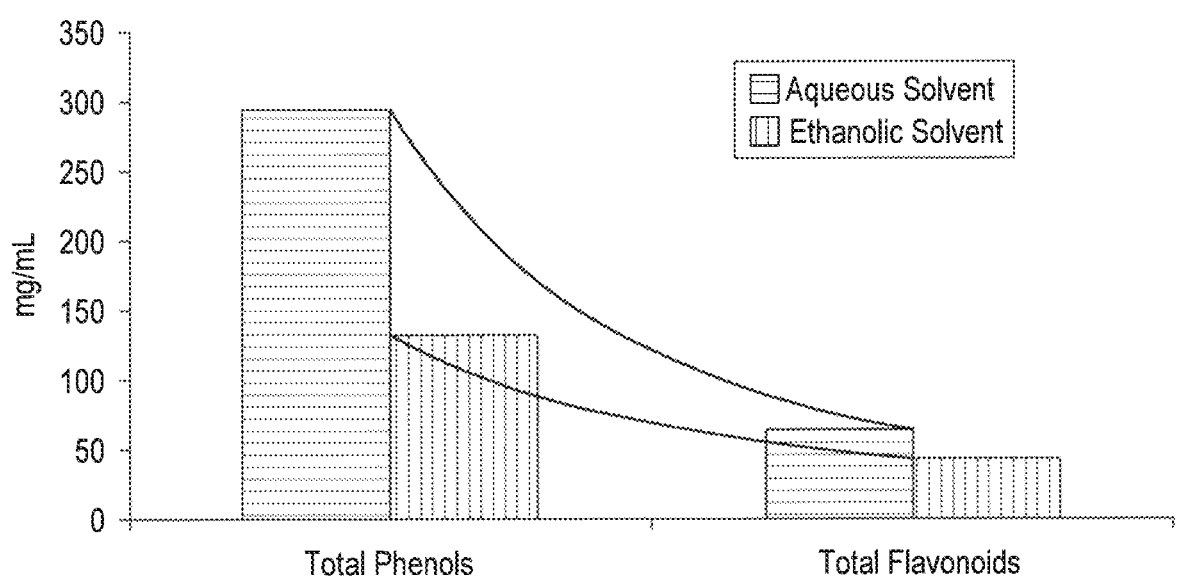
FIG. 1 depicts a bar graph illustrating the antioxidant activity of olive leaf aqueous extracts extracted with water vs. extracted with ethanol.
Figure 2A:
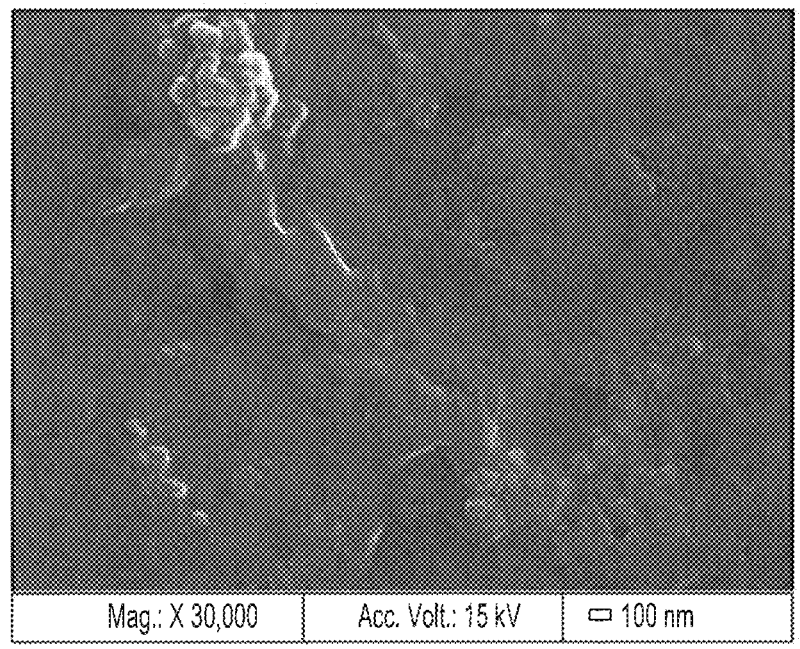
FIG. 2A depicts a scanning electron micrograph of the olive leaf extract AgNPs adhesion to breast cancer cells of cell line MCF-7.
Figure 2B:
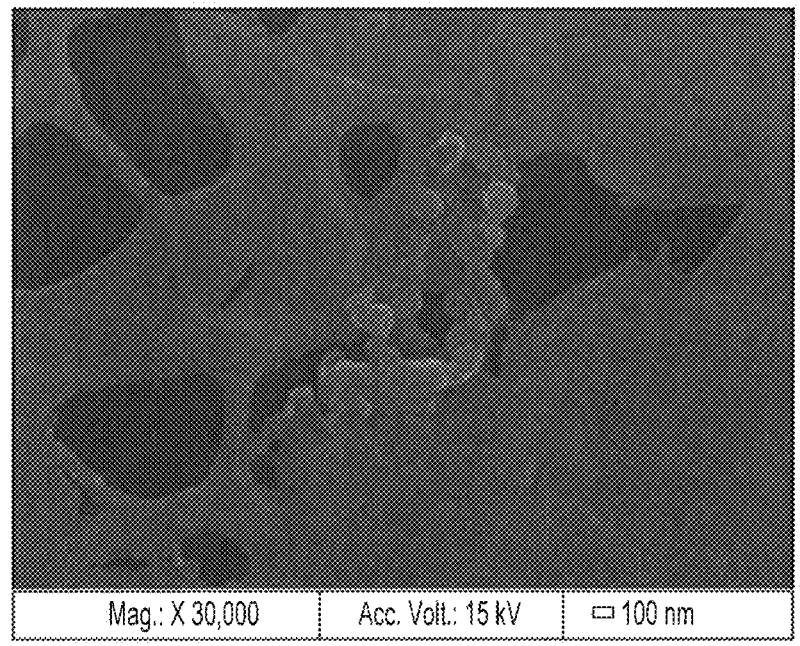
FIG. 2B depicts a scanning electron micrograph of the olive leaf extract AgNPs adhesion to breast cancer cells of cell line SKBr3.
Figure 2C:
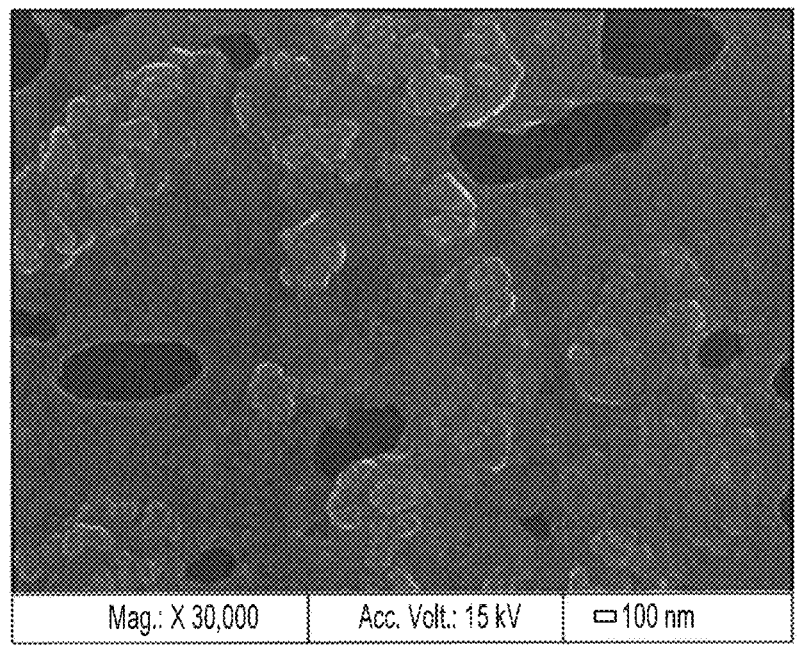
FIG. 2C depicts a scanning electron micrograph of the olive leaf extract AgNPs adhesion to breast cancer cells of cell line AMJ13.
Figure 2D:
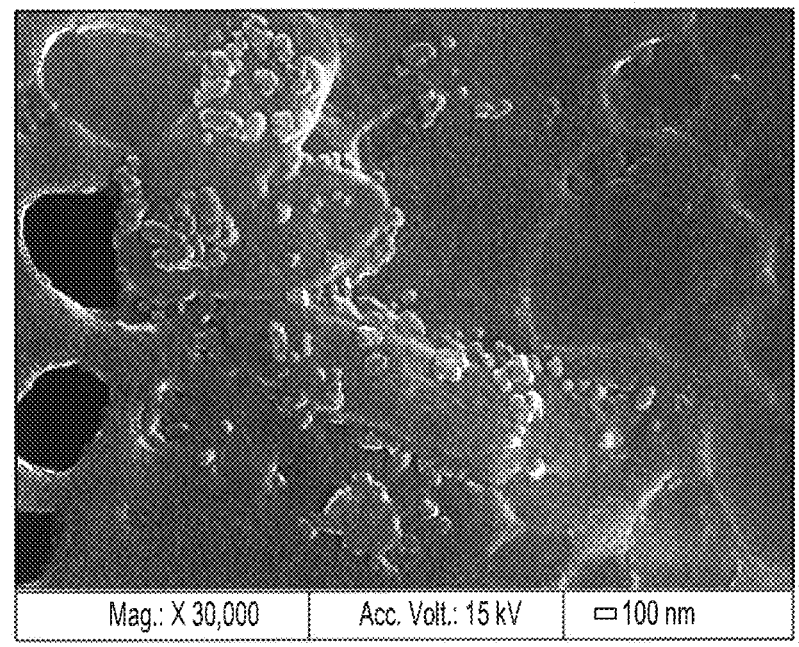
FIG. 2D depicts a scanning electron micrograph of the olive leaf extract AgNPs adhesion to breast cancer cells of cell line MDA-MB-231.

Synthesis of olive leaf extract silver nanoparticles may include extracting olive leaves, e.g., leaves from the plant *Olea europaea* L., to provide an olive leaf extract and using the olive leaf extract to synthesize olive leaf extract AgNPs. The method of synthesizing olive leaf extract may include harvesting or collecting olive leaves and washing the olive leaves. The washed olive leaves may be dried and ground to form an olive leaf powder. In an embodiment, the olive leaf powder is mixed with a liquid or extract solution to form an extract. In one embodiment, the extract solution may include water, and the ratio of olive leaf powder to extract solution may be 1:10. In an alternative embodiment, the extract solution may include ethanol, and the ratio of olive leaf powder to extract solution may be 1:20. The extract solution and olive leaf powder may be mixed and allowed to sit at room temperature to form a first olive leaf extract. The first olive leaf extract may then be separated and/or concentrated by centrifugation and filtration to provide a filtrate. The filtrate can be evaporated to provide a residue. The residue may then be resuspended in a solvent, e.g., ethanol, to provide a final olive leaf extract. The olive leaf extract may then be used to synthesize olive leaf extract AgNPs by mixing the final olive leaf extract with silver nitrate ($AgNO_3$) to form a mixture including olive leaf extract AgNPs. The nanoparticles can be separated from the mixture by centrifugation. In an embodiment the olive leaves may be olive leaves grown in the Al-Jouf region of Saudi Arabia.

As used herein, a "subject" includes mammals, e.g., humans, dogs, cats, sheep, cows, rats, mice and the like.

As used herein, the term "about," when used to modify a numerical value, means within ten percent of that numerical value.

An embodiment of the present subject matter is directed to a pharmaceutical composition comprising the olive leaf extract AgNPs and a pharmaceutically acceptable carrier.

An embodiment of the present subject matter is directed to a method of making a pharmaceutical composition including mixing the olive leaf extract AgNPs with a pharmaceutically acceptable carrier. For example, the method of making a pharmaceutical composition can include mixing the probiotic nanoparticles under sterile conditions with a pharmaceutically acceptable carrier with preservatives, buffers, and/or propellants to create the pharmaceutical composition.

An embodiment of the present subject matter is directed to a pharmaceutical composition including the olive leaf extract AgNPs. To prepare the pharmaceutical composition, the olive leaf extract AgNPs, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the olive leaf extract AgNPs or an amount effective to treat a disease, such as a cancer, may be determined initially from the Examples described herein and adjusted for specific targeted diseases using routine methods.

The olive leaf extract AgNPs can be administered to a subject in need thereof. The olive leaf extract AgNPs can provide antioxidant activity. In an embodiment, the olive leaf extract AgNPs can be used to treat a subject suffering from a disease such as cancer. In a further embodiment, the disease can be breast cancer.

An embodiment of the present subject matter is directed to a method of treating cancer, comprising administering to a subject in need thereof a therapeutically effective amount of the pharmaceutical composition according to the present subject matter.

The olive leaf extract AgNPs or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The olive leaf extract may be prepared by collecting leaves of an olive plant for use as the extraction substrate. The leaves may then be washed, dried, and a desired amount may be ground to form an olive leaf powder. The olive leaf powder may be placed in a container with an aqueous solvent and kept at room temperature to form an extract. The extract may then be separated and/or concentrated by centrifugation, filtration, and evaporation. In an embodiment, the aqueous solvent may be selected from the group consisting of water and ethanol. In an embodiment, the centrifugation may be performed at 16,000×G for about 10 minutes at about 4° C. In an embodiment, the filtration may use a 0.45 μm syringe filter. In an embodiment, the evaporation may be performed in a rotary evaporator, and the resulting residue may be suspended in ethanol, for use as an olive leaf extract.

Green synthesis of olive leaf extract AgNPs may be achieved by mixing at least one olive leaf extract with silver nitrate and incubating the mixture at room temperature until the color of the mixture darkens, indicating the production of AgNPs.

In an embodiment, the olive leaf extract AgNPs synthesis may include mixing the olive leaf extract with the $AgNO_3$ at a 1:10 ratio. In a further embodiment, the olive leaf extract AgNPs synthesis may include mixing about 1 ml of the at least one olive leaf extract with about 10 ml of $AgNO_3$.

Separation and/or concentration of the olive leaf extract AgNPs may be achieved by centrifuging the olive leaf extract and $AgNO_3$ mixture. In a non-limiting example, the centrifuging may be performed at 8,000 rpm for about 20 minutes, producing a pellet. The pellet may then be washed by resuspending the pellet in distilled water and repeating the centrifuging step. The washed pellet may then be air dried, providing olive leaf extract AgNPs.

In an embodiment, the olive leaf extract AgNPs may be synthesized using the leaves of the olive plant *Olea europaea* L.

In embodiment, the olive plants used to synthesize the olive leaf extract AgNPs may be grown in the Al-Jouf region of Saudi Arabia.

In an embodiment, the olive leaf extract AgNPs may be spherical in shape and have a size ranging from about 20 nm and about 40 nm.

Plant mediated production of nanoparticles provides a green and/or renewable method of synthesis, which is preferred over chemical synthesis. In the present work olive leaf extract served as a stable capping agent. The formation of AgNPs using olive leaf extract may in part relate to biomolecular bonds mediated by hydrogen bonds and electrostatic interactions.

The following examples illustrate the present subject matter.

Example 1

Synthesis of Olive Leaf Extracts

Fresh green leaves of olive trees (*Olea europaea* L.) were harvested and collected from the Al-Jouf area in Saudi Arabia. The olive leaves were washed to remove impurities and air dried for two days at room temperature. The dried leaves were ground into a fine olive leaf powder. Extraction of the olive leaf powder was carried out using two solvents: water and ethanol. Olive leaf powder was extracted with 100 mL of distilled water or 100 mL of ethanol at respective ratios of 1:10 and 1:20. The extraction was performed at room temperature (20° C.) and crude extracts with two different molecular weights were obtained based on solvent type; 157.32 mg/mL in the aqueous solvent and 59.2 mg/mL, in the ethanolic solvent. The crude extracts were centrifuged at 4° C. (approx. 16,000×g, for 10 minutes), filtered through a 0.45 μm syringe filter, and supernatants were separated into new fresh glass tubes. The filtrates were evaporated to dryness in a rotary evaporator (Labconco Corp.) and the residue was dissolved in ethanol and stored at −20° C. until subjected to polyphenol analyses.

Example 2

Polyphenol Analysis of Olive Leaf Extracts

Total phenolic and flavonoid contents of the olive leaf extracts synthesized according to Example 1 were estimated using LC-MS-MS. 0.5 mL of the extract was lyophilized, then reconstituted in 0.5 ml of mobile phase (1 mL of acetic acid in 1 L of $H_2O$ and 500 mL of acetonitrile in 500 mL of methanol) prior to LC-MS-MS analysis. The total phenolics and flavonoids of the olive leaf extracts (aqueous and ethanolic) were 293.32 mg/mL, 64.73 mg/mL, 132.9 mg/mL, and 43.52 mg/mL respectively.

The signature for AgNP formation was confirmed by absorption peaks between 410 to 470 nm.

FIG. 1 illustrates the yield of phenolic and flavonoid compounds extracted by the aqueous solvent and the ethanolic solvent, respectively. The range of compounds identified by LC-MS-MS analysis of olive leaf extract are presented in Table 1. A total of 14 phenolic compounds were detected and identified.

TABLE 1

Olive leaf extract Phenolic and Flavonoid Compounds Identified by LC-MS-MS

| Identified compound | MS fragments m/z | Molecular weight | Formula |
| --- | --- | --- | --- |
| Oleuropein aglycone | 378.377 | 377.1254 | $C_{19}H_{22}O_8$ |
| Oleuropein | 540.510, 539.169 | 540.51 | $C_{25}H_{32}O_{13}$ |
| Rutin | 610.52 | 610.52 | $C_{27}H_{30}O_{16}$ |
| Tyrosol | 138.164 | 138.16 | $C_8H_{10}O_2$ |
| Apigenin | 267.121, 340 | 270.05 | $C_{15}H_9O$ |
| Hydroxytyrosol | 123.102 | 154.17 | $C_8H_{10}O_3$ |
| Carboxymethylated | 182.6, 398.88 | 378.00 | $C_8H_{16}O_8$ |
| AFOA | 260.2, 301.3, 323.12 | 378.00 | —OH |
| Hydroxytyrosyl acetate | 138.71 | 196.00 | $C_{10}H_{12}O_4$ |
| Vanillic acid | 279.436 | 168.15 | $C_8H_8O_4$ |
| AFLA | 442.5, 589.2 | 362.00 | $C_6H_5OH$ |
| Pinoresinol | 359.642, 345.231 | 415.00 | $C_{20}H_{21}O_6$ |
| Luteolin | 311.224, 283.312 | 286.00 | $C_{15}H_9O_6$ |
| Acetoxypinoresinola | 415.202 | 358.39 | $C_{22}H_{23}O_8$ |

Example 3

Synthesis of Olive Leaf Extract AgNPs

Olive leaf aqueous extract (1 mL) was mixed with 10 mL of 2 mM silver nitrate ($AgNO_3$) solution in a dark chamber at room temperature (20° C.), forming a mixture. The formation of $AgNO_3$ nanoparticles in solution was confirmed by color change of the mixture from colorless to dark brown. The colloidal solution was centrifuged (8000 rpm) for 20 min. Pellets were resuspended in distilled water and centrifuged again for removing impurities. The pellets were air dried to produce olive leaf AgNPs and particle size and morphology was analyzed using scanning electron microscopy (SEM).

Example 4

Characteristics of Olive Leaf Extract AgNPs

The olive leaf AgNPs synthesized according to Example 3 were characterized using UV-Vis spectroscopy via scanning the spectra at a wavelength of 200-700 nm. The signature of AgNP formation was confirmed, as an absorption peak was detected in the region of 410 to 470 nm. The synthesized nanoparticles were characterized by scanning electron microscopy (SEM) and were found to be spherical in shape with a size ranging from 20-40 nm (See FIGS. 2A-2D).

Example 5

Antioxidant Activity of Olive Leaf Extract AgNPs

The DPPH (2,2-diphenyl-1-picryl-hydrazyl-hydrate) free radical method was used to determine the antioxidant activity of olive leaf AgNPs. Equal volumes (0.5 mL) of DPPH solution (60 μM) and olive leaf AgNPs (at concentration of 100, 200, 300, 400 and 500 μg/mL) were mixed in a cuvette and allowed to settle at room temperature for 30 min. The olive leaf AgNPs (sample) and DPPH were dissolved in ethanol. The DPPH radical without sample and with ascorbic acid was used as a positive control. Absorbance was read at a wavelength of 520 nm in a UV-Vis spectrophotometer. The percentage of DPPH decoloration of the samples was calculated to measure the free radical scavenging activity of the olive leaf AgNPs. The percentage of DPPH decolouration was calculated according to the following formula:

% DPPH decoloration=(Abs Control−Abs Sample/ Abs Control)×100

Figure 3:
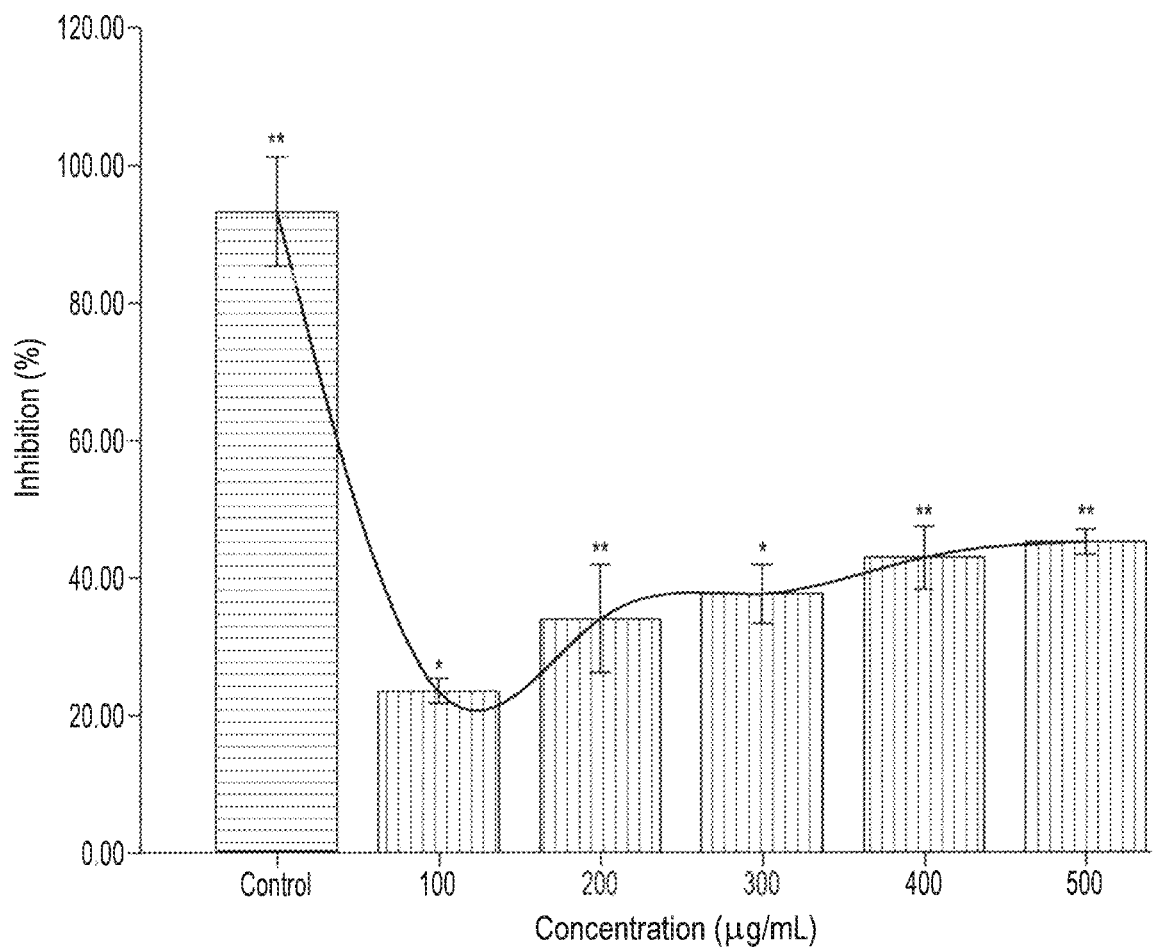
FIG. 3 depicts a bar graph illustrating antioxidant activity of olive leaf extract AgNPs.

The antioxidant activity of olive leaf extract AgNPs was dose dependent, with DPPH free radical scavenging increasing with the concentration of olive leaf extract AgNPs, as revealed by percent decolouration of DPPH. The $IC_{50}$ is described as amount of sample required to scavenge 50% of DPPH free radicals. The $IC_{50}$ value for olive leaf extract AgNPs was 18.22 μg/mL, revealing a strong antioxidant activity (FIG. 3). A lower $IC_{50}$ value indicates high antioxidant activity. This high antioxidant activity of olive leaf extract AgNPs may result from the presence of phenolic compounds found in the olive leaf extract. The least information criteria of mean percentage inhibition according to Akaike's information criterion (AIC) and Hurvich and Tsai's criterion (AICC) was 789.614 ($R^2$=0.45). Interpolation of different concentrations of olive leaf extract AgNPs relative to control showed significant free radical scavenging activity in a dose dependent manner. The maximum antioxidant activity (45.1%) was achieved at a concentration of 500 μg/mL olive leaf extract AgNPs. The antioxidant activity of olive leaf extract AgNPs is summarized in FIG. 3.

Example 6

Anticancer Activity of Olive Leaf Extract AgNPs

The anticancer activity of olive leaf extract AgNPs was tested on human breast cancer cell lines MCF7, SKBr3, AMJ13 and MDA-MB-231. The cell lines were cultured on 96 well-plates ($1\times10^5$ cells/well) in Dulbecco's modification of Eagle's medium (DMEM) containing 1% L-glutamine, 10% fetal bovine serum, 100 units/mL penicillin and 100 μg/mL streptomycin. Cells were maintained in a humidified atmosphere containing 5% $CO_2$ at 37° C. After 24 hours of incubation, the cells were treated with different concentrations of the olive leaf extract AgNPs followed by further incubation for 24 h. Cells incubated with water without olive leaf extract AgNPs served as a control. FIG. 3 shows aggregation and clumping of AgNPs on breast cancer cell lines after 24 h of incubation.

The putative anticancer activity of the olive leaf extract AgNPs against human tumor cell lines was determined using tetrazolium salt-based (MTT) cell viability assay. This assay is based on the principle of reduction of 3-(4,5-dimethylthiazol-2-yl)-2,5-diphenyltetrazolium bromide (MTT) to formazan. The olive leaf extract AgNP treated cells were incubated with a solution of MTT for 4 h at 37° C. The MTT solution was prepared in PBS at a concentration of 5 mg/mL. Formazan crystals produced in wells containing live cells appeared as black crystals on the well bottom. The formazan crystals were resuspended and dissolved in 100 μL DMSO added to each well. Viable cells were measured by microplate plate reader with a test wavelength of 570 nm and a reference wavelength of 630 nm (Bio-Rad, Richmond, Calif.). This measurement was performed in triplicate. The percent cell viability was calculated using the formula:

$$\% \text{ Cell Viability} = \left( \frac{1 - A570 \text{ Treated Tumor Cells}}{A570 \text{ Non} - \text{Tumor Cells}} \right) 100\%$$

The results of these MTT experiments are expressed as the mean of three to six replicates. $IC_{50}$ value were calculated as the concentration of Olive leaf extract AgNPs required to decrease 50% of cell viability (See FIG. 4).

Approximately 250,000 cells were cultured onto glass slides for 8 h and treated with the olive leaf extract AgNPs (50 μg/mL) for 24 h. Untreated and treated cells were washed with 1 mL/well of cold phosphate-buffered saline (PBS) twice. The cells were fixed with cold 3.7% paraformaldehyde, followed by washing with cold phosphate-buffered saline (PBS) twice. The cells were stained with 1 μg/ml, 4'-6-diamidino-2-phenylindole (DAPI) for 5 minutes. The stained cells were rinsed with PBS, and the cells were examined under inverted phase contrast microscopy (Nikon Eclipse TS100, Nikon, Tokyo, Japan).

Data obtained from the experiments were pooled and analyzed using SPSS version-25. One-way analysis of variance (ANOVA) was used and equal variances were assumed through LSD and DMRT. Values were expressed as mean±SD with p-value less than 0.05 and 0.01 were considered as statistically significant. Means were further tested using Akaike's information criterion (AIC) and Hurvich and Tsai's criterion.

Figure 4:
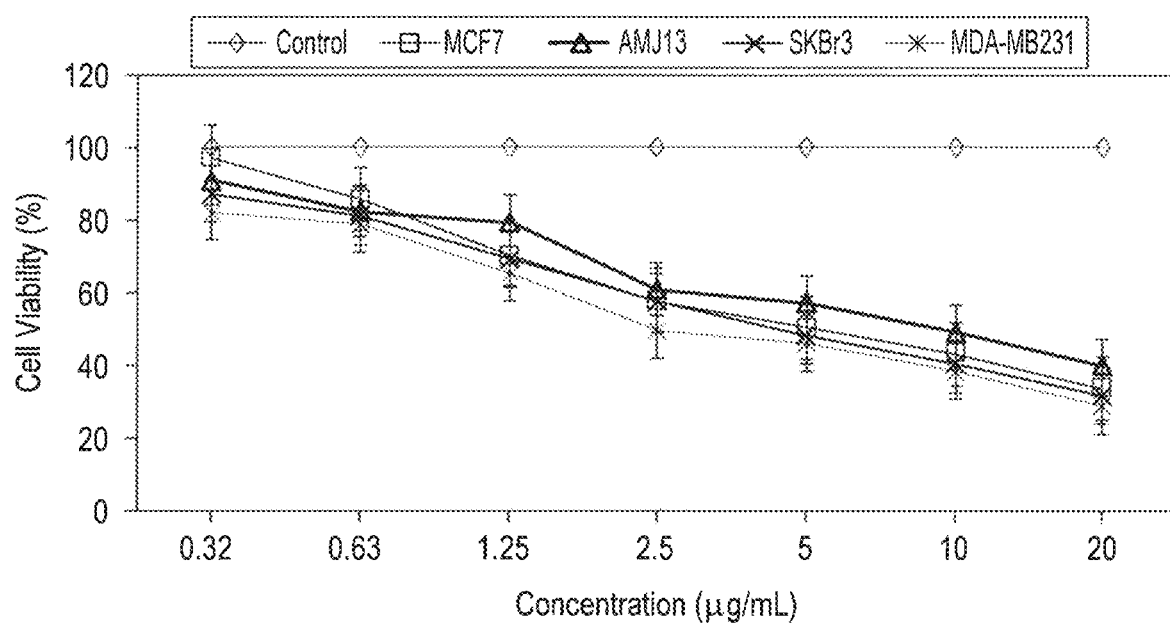
FIG. 4 depicts a line graph of the cytotoxic activity of olive leaf extract AgNPs on breast cancer cell lines.
Figures 5A, 5B, 5C, 5D:
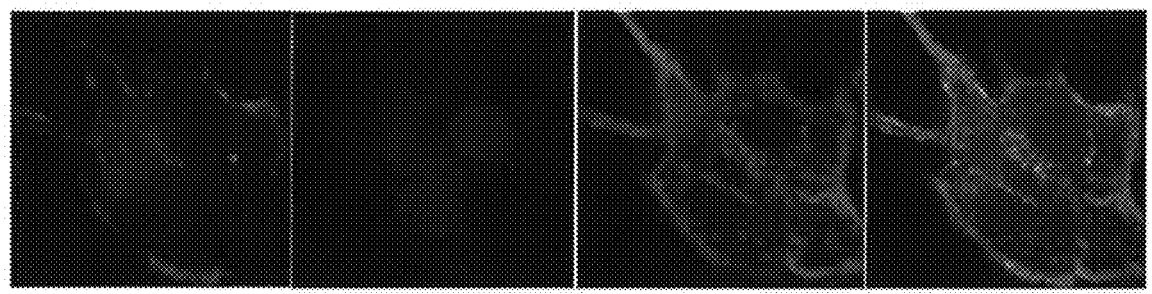
FIG. 5A depicts a fluorescent micrograph of untreated MCF-7 cells.
FIG. 5B depicts a fluorescent micrograph of untreated MCF-7 cells.
FIG. 5C depicts a fluorescent micrograph of MCF-7 cells treated with olive leaf extract AgNPs.
FIG. 5D depicts a fluorescent micrograph of MCF-7 cells treated with olive leaf extract AgNPs.
Figures 6A, 6B, 6C, 6D:
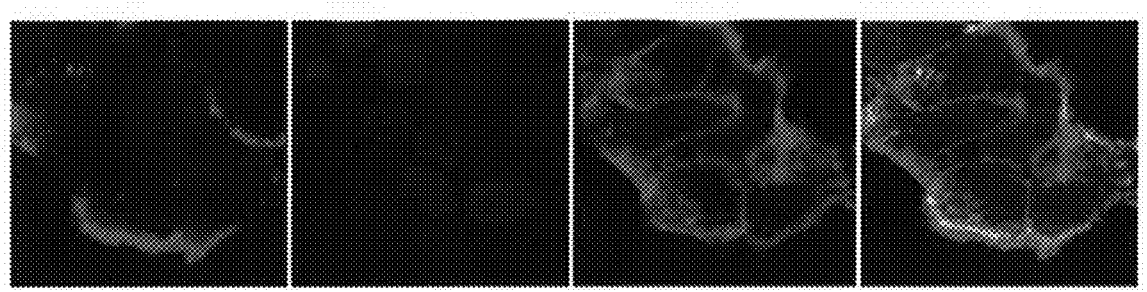
FIG. 6A depicts a fluorescent micrograph of untreated SKBr3 cells.
FIG. 6B depicts a fluorescent micrograph of untreated SKBr3 cells.
FIG. 6C depicts a fluorescent micrograph of SKBr3 cells treated with olive leaf extract AgNPs.
FIG. 6D depicts a fluorescent micrograph of SKBr3 cells treated with olive leaf extract AgNPs.
Figures 7A, 7B, 7C, 7D:
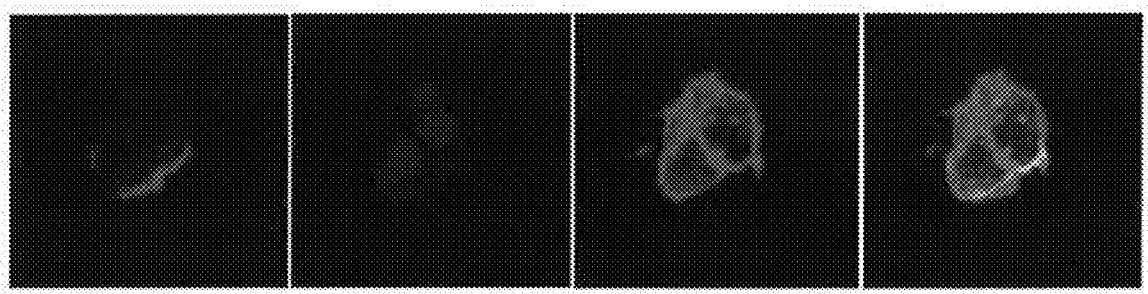
FIG. 7A depicts a fluorescent micrograph of untreated AMJ13 cells.
FIG. 7B depicts a fluorescent micrograph of untreated AMJ13 cells.
FIG. 7C depicts a fluorescent micrograph of AMJ13 cells treated with olive leaf extract AgNPs.
FIG. 7D depicts a fluorescent micrograph of AMJ13 cells treated with olive leaf extract AgNPs.
Figures 8A, 8B, 8C, 8D:
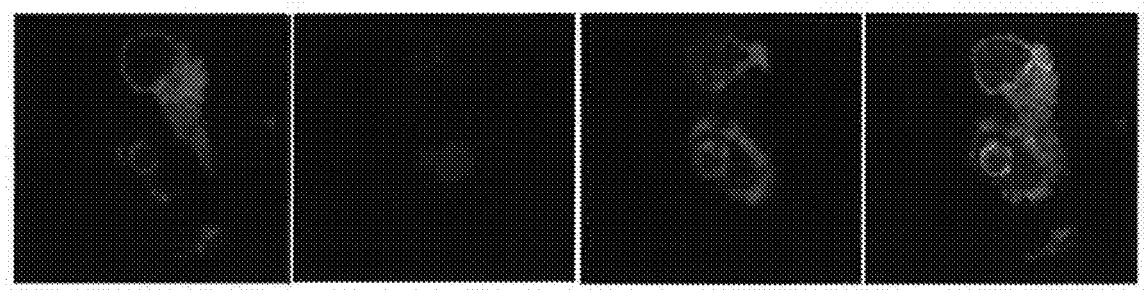
FIG. 8A depicts a fluorescent micrograph of untreated MDA-MB-231 cells.
FIG. 8B depicts a fluorescent micrograph of untreated MDA-MB-231 cells.
FIG. 8C depicts a fluorescent micrograph of MDA-MB-231 cells treated with olive leaf extract AgNPs.
FIG. 8D depicts a fluorescent micrograph of MDA-MB-231 cells treated with olive leaf extract AgNPs.

Anticancer effects of olive leaf extract AgNPs on MCF7, AMJ13, SKBr3 and MDA-MB-231 breast cancer cell lines were examined by MTT assay. A concentration dependent cytotoxicity was observed (as illustrated in FIG. 4). As the concentration of AgNPs increased, the percentage of cell viability and cell proliferation of MCF7, AMJ13, SKBr3 and MDA-MB-231 breast cancer cell lines decreased. The cells were mostly unresponsive at a concentration of 0.32 μg/mL. However, sensitivity increased with the increase in concentration from 0.63 μg/mL to 20 μg/mL as exhibited by decreased cell proliferation. The tumoricidal effects were more pronounced in AMJ13 breast cancer cell lines at concentrations ranging from 10 μg/mL to 20 μg/mL. The least inhibitory effect was noted on MDA-MB231 breast cancer cell lines. $IC_{50}$ values of olive leaf extract AgNPs against MCF7, AMJ13, SKBr3 and MDA-MB-231 cells are 51.6, 54, 42.3 and 32.3 μg/mL respectively.

The effects of olive leaf extract AgNPs on MCF7, SKBr3, AMJ13 and MDA-MB-231 cell lines were also evaluated using inverted phase contrast microscopy. FIGS. 5A-8D illustrate morphological changes that occurred in tumor cell lines at concentrations of 50 μg/mL of olive leaf extract AgNPs. DAPI staining shows altered nuclear shape, and/or neighboring DNA fragments of the nuclei. DAPI staining shows the location of stained DNA in blue in FIGS. 5A-8D. Untreated control cells exhibited normal healthy shape with visible round nucleus. The treated cells show altered cell and nuclear shape, and/or neighboring DNA fragments and orange to red nuclei.

It is to be understood that the synthesis of olive leaf extract silver nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing olive leaf extract silver nanoparticles, comprising:
    providing olive leaves;
    grinding the olive leaves to provide an olive leaf powder;
    mixing the olive leaf powder with a first solvent to form a first olive leaf extract;
    concentrating the first olive leaf extract to provide a filtrate, wherein concentrating the first olive leaf extract to provide a filtrate comprises:
        i) centrifuging the first olive leaf extract at about 16,000×G, at a temperature of 4° C., for about 10 minutes to provide a pellet; and
        ii) filtering the pellet through a 0.45 μm syringe filter to provide the filtrate;
    evaporating the filtrate to provide a residue;
    dissolving the residue in a second solvent to provide a final olive leaf extract; and
    mixing the final olive leaf extract with $AgNO_3$ to form a mixture including the silver nanoparticles.

2. The method of synthesizing olive leaf extract silver nanoparticles of claim 1, wherein the first solvent and the second solvent are independently selected from the group consisting of water and ethanol.

3. The method of synthesizing olive leaf extract silver nanoparticles of claim 1, wherein the olive leaves are leaves of the plant *Olea europaea* L.

4. The method of synthesizing olive leaf extract silver nanoparticles of claim 3, wherein the olive leaves are grown in the Al-Jouf region of Saudi Arabia.

5. The method of synthesizing olive leaf extract silver nanoparticles of claim 1, wherein about 1 ml of the final olive leaf extract is mixed with about 10 ml of $AgNO_3$.

6. Olive leaf extract silver nanoparticles synthesized according to claim 1.

7. The olive leaf extract silver nanoparticles of claim 6, wherein the olive leaf extract silver nanoparticles are spherical.

8. The olive leaf extract silver nanoparticles of claim 7, wherein the olive leaf extract silver nanoparticles range from about 20 nm to about 40 nm in size.

9. A method of treating cancer in a subject by administering an effective amount of the olive leaf extract silver nanoparticles of claim 6.

10. The method of claim 9, wherein the cancer is breast cancer.

11. A pharmaceutical composition comprising the olive leaf extract silver nanoparticles according to claim 6 and a pharmaceutically acceptable carrier.

* * * * *